United States Patent
Kawachi et al.

(10) Patent No.: US 9,556,098 B2
(45) Date of Patent: Jan. 31, 2017

(54) REDUCED COENZYME Q10 CRYSTAL HAVING EXCELLENT STABILITY

(71) Applicant: KANEKA CORPORATION, Osaka-shi (JP)

(72) Inventors: Hideo Kawachi, Hyogo (JP); Shiro Kitamura, Hyogo (JP); Yasuyoshi Ueda, Hyogo (JP)

(73) Assignee: KANEKA CORPORATION, Osaka-shi (JP)

( * ) Notice: Subject to any disclaimer, the term of this patent is extended or adjusted under 35 U.S.C. 154(b) by 0 days.

(21) Appl. No.: 15/181,511

(22) Filed: Jun. 14, 2016

(65) Prior Publication Data

US 2016/0289152 A1 Oct. 6, 2016

Related U.S. Application Data

(63) Continuation of application No. 14/129,003, filed as application No. PCT/JP2012/065869 on Jun. 21, 2012, now Pat. No. 9,388,109.

(30) Foreign Application Priority Data

Jun. 24, 2011 (JP) ................. 2011-141028

(51) Int. Cl.
- A61K 31/122 (2006.01)
- C07C 49/577 (2006.01)
- A61K 9/28 (2006.01)
- A23L 2/52 (2006.01)
- A23L 1/30 (2006.01)

(52) U.S. Cl.
CPC ................ *C07C 49/577* (2013.01); *A23L 1/30* (2013.01); *A23L 2/52* (2013.01); *A61K 9/28* (2013.01); *A61K 31/122* (2013.01); *A23V 2002/00* (2013.01)

(58) Field of Classification Search
CPC ...................................... A61K 9/28
See application file for complete search history.

(56) References Cited

U.S. PATENT DOCUMENTS

| | | |
|---|---|---|
| 6,184,255 B1 | 2/2001 | Mae et al. |
| 7,358,402 B2 | 4/2008 | Ueda et al. |
| 2004/0197418 A1 | 10/2004 | Ueda et al. |
| 2004/0197886 A1 | 10/2004 | Ueda et al. |
| 2004/0214301 A1 | 10/2004 | Ueda et al. |
| 2004/0215040 A1 | 10/2004 | Ueda et al. |
| 2005/0008630 A1 | 1/2005 | Ueda et al. |
| 2005/0074860 A1 | 4/2005 | Ueda et al. |
| 2006/0246565 A1 | 11/2006 | Ueda et al. |
| 2009/0088574 A1 | 4/2009 | Urawa et al. |

FOREIGN PATENT DOCUMENTS

| | | |
|---|---|---|
| CN | 1525951 A | 9/2004 |
| CN | 1527807 A | 9/2004 |
| CN | 1551862 A | 12/2004 |
| CN | 1599603 A | 3/2005 |
| CN | 1723181 A | 1/2006 |
| CN | 1266101 C | 7/2006 |
| EP | 1 415 969 A1 | 5/2004 |
| JP | 10 109933 | 4/1998 |
| JP | 2003 089669 | 3/2003 |
| JP | 2006 513274 | 4/2006 |
| WO | 03 006408 | 1/2003 |
| WO | 03 006409 | 1/2003 |
| WO | 03 006411 | 1/2003 |
| WO | 03 008363 | 1/2003 |
| WO | 03 032967 | 4/2003 |
| WO | 2005 033054 | 4/2005 |
| WO | 2007 072868 | 6/2007 |

OTHER PUBLICATIONS

International Search Report Issued Jul. 24, 2012 in PCT/JP12/065869 filed Jun. 21, 2012.
Brittain "Polymorphism in pharmaceutical solids" 1999, Marcel Dekker, p. 178-179, 219, 185.
Extended European Search Report issued Nov. 3, 2014 in Patent Application No. 12802693.7 filed Jun. 21, 2012.
Combined Chinese Office Action and Search Report issued Sep. 25, 2014 in Patent Application No. 201280031157.X with English Translation of Category of Cited Documents.

*Primary Examiner* — Yong Chu
*Assistant Examiner* — Ana Z Muresan
(74) *Attorney, Agent, or Firm* — Oblon, McClelland, Maier & Neustadt, L.L.P.

(57) ABSTRACT

With respect to reduced coenzyme Q10, there has been no report about the presence of crystal polymorphism, and it has been considered that a conventionally obtained crystal form is only one form. The present invention relates to a reduced coenzyme Q10 crystal having an endothermic peak indicating melting at 54±2° C. during temperature rise at a rate of 5° C./min by differential scanning calorimetry (DSC), and/or to a reduced coenzyme Q10 crystal showing characteristic peaks at diffraction angles (2θ±0.2°) of 11.5°, 18.2°, 19.3°, 22.3°, 23.0° and 33.3° by powder X-ray (Cu—Kα) diffraction. The crystal form is a novel reduced coenzyme Q10 crystal which has a higher melting point and a lower solubility in a solvent, and is more excellent in stability than the conventionally known reduced coenzyme Q10 crystal.

12 Claims, 4 Drawing Sheets

REDUCED COENZYME Q10 CRYSTAL HAVING EXCELLENT STABILITY

CROSS-REFERENCE TO RELATED APPLICATIONS

The present application is a continuation of U.S. application Ser. No. 14/129,003, filed Dec. 23, 2013, which is a national stage of International Application No. PCT/JP2012/065869, filed Jun. 21, 2012, which is based upon and claims the benefits of priority to Japanese Application No. 2011-141028, filed Jun. 24, 2011. The entire contents of all of the above applications are incorporated herein by reference.

TECHNICAL FIELD

The present invention relates to a reduced coenzyme Q10 crystal excellent in stability, a reduced coenzyme Q10 crystalline solid containing the crystal, and a method for the production thereof, use thereof and a composition containing the same. Reduced coenzyme Q10 exhibits higher oral absorbability than that of oxidized coenzyme Q10, and is a compound useful for good foods, nutritional functional foods, specified health foods, nutritious supplements, nutrients, animal drugs, drinks, feeds, cosmetics, medicaments, treating drugs, preventing drugs, pet foods, or the like.

BACKGROUND ART

Coenzyme Q is an essential component widely distributed in living organisms from bacteria to mammals, and is known as a component of mitochondrial electron transfer system in cells in the living body. Coenzyme Q serves as a transfer component in the electron transfer system by the repetition of oxidation and reduction in mitochondria, and, further, reduced coenzyme Q is known to have antioxidant activity. The major component in humans is coenzyme Q10 which is one having 10 isoprenoid repeating structures in its side chain, and, usually, about 40 to 90% thereof is present in the living body as the reduced form. The physiological activity of coenzyme Q includes activation of energy production by mitochondrial activation, activation of cardiac function, an effect of stabilizing cell membranes, and an effect of protecting cells by antioxidant activity.

While coenzyme Q10 currently produced and sold is, in large part, oxidized coenzyme Q10, reduced coenzyme Q10 which exhibits higher oral absorbability than that of oxidized coenzyme Q10 has also been commercially available and has come to be used in recent years.

Patent Literature 1 discloses a common method for obtaining reduced coenzyme Q10. Furthermore, several methods for obtaining reduced coenzyme Q10 as a crystal are also known. For example, in Patent Literature 2, reduced coenzyme Q10 is produced as a crystal by crystallization in an alcohol solution and/or a ketone solution. In Patent Literature 3, reduced coenzyme Q10 is crystallized by adding the high concentration liquid phase thereof to a poor solvent.

In addition, Patent Literature 4 discloses that reduced coenzyme Q10 is dissolved in oil and fat and then cooled, thereby making it possible to yield a crystal which has a different X-ray diffraction pattern from that of a usual reduced coenzyme Q10 crystal and is excellent in stability.

Reduced coenzyme Q10 is known to usually have a property such that it is easily oxidized in the presence of molecular oxygen to be converted into oxidized coenzyme Q10. In response, for example, Patent Literature 5 discloses, as a method for stabilizing reduced coenzyme Q10, a method for allowing reduced coenzyme Q10 to contact and coexist with ascorbic acids or citric acids. In addition, the conventional reduced coenzyme Q10 crystal has the property of being very easily electrostatically charged.

By the way, it has been reported for many compounds, whether organic compounds or inorganic compounds, that a plurality of crystal forms having different crystal structures are generally present, which are called "crystal polymorphs". A plurality of crystal forms in a crystal polymorphism each show different patterns in analysis such as X-ray diffraction or infrared spectroscopic analysis, as well as have different physical properties such as melting point and solubility. In general, there is a tendency that a more energetically stable crystal form under the defined conditions has a higher melting point and a lower solubility, and a crystal form having the highest melting point and the lowest solubility is usually called "stable form". In the case of a crystal form other than the stable form, transition to the stable form can occur during operation such as crystallization, drying, or pulverization. The transition is a very natural phenomenon that a substance changes toward an energetically stable state, but physical properties of the resulting crystal also change due to such a phenomenon, thereby possibly causing the crystal or a formulation containing such a crystal as an active ingredient to have problems in terms of quality. The crystal in the stable form not only causes no such transition but also has a high melting point as described above, thereby making it possible to be dried at a higher temperature during drying thereof, and has a low solubility, thereby making it possible to yield a crystal in a larger amount during crystallization, and, therefore, has an advantage of increasing efficiency at the time of production. For such reasons, in the case where a compound whose crystal polymorphs are present is utilized for, in particular, medical applications or the like, it is important to select an optimal crystal form such as the stable form.

It has also been reported that different crystal forms have different electrostatic charges. If a crystal takes an electrostatic charge, its sticking to equipment at the time of production, or the like, not only decreases the efficiency at the production but also causes problems in terms of safety, such as dust explosion and contamination of facilities/workers. In the case of a compound having crystal polymorphs, selecting the optimal crystal polymorph can be one effective measure against the above problems. For example, in Patent Literature 6, it has been reported that a new crystal form (type IV) of a 1,2-dihydropyridine compound has a lower electrostatic charge than other crystal forms.

CITATION LIST

Patent Literatures

Patent Literature 1: JP Patent Publication (Kokai) No. 10-109933 (1998)
Patent Literature 2: JP Patent Publication (Kokai) No. 2003-006409
Patent Literature 3: JP Patent Publication (Kokai) No. 2003-089669
Patent Literature 4: WO2005/033054
Patent Literature 5: WO2003/032967
Patent Literature 6: WO2007/072868

SUMMARY OF INVENTION

Technical Problem

As described above, while it has been found that many compounds have crystal polymorphs, no crystal polymorph of reduced coenzyme Q10 has been reported to be clearly identified, and it is considered that the crystal form which has been conventionally obtained is only one crystal form. Accordingly, for the enhancement in physical properties, studies have been made to devise a combination with a component simultaneously used and a method for obtaining a formulation.

Solution to Problem

The present inventors have made intensive studies in view of the circumstances. As a result, they have first found that a new crystal form is present which has a different crystal structure from that of the conventionally known reduced coenzyme Q10 crystal, namely, the crystal polymorphism of reduced coenzyme Q10 is present, and further, have confirmed that the new crystal form is a more stable crystal form than that of the conventionally known crystal, thereby leading to the completion of the present invention.

That is, the present invention relates to a reduced coenzyme Q10 crystal having an endothermic peak at 54±2° C. during temperature rise at a rate of 5° C./min by differential scanning calorimetry (DSC).

In addition, the present invention relates to a reduced coenzyme Q10 crystal showing characteristic peaks at diffraction angles (2θ±0.2°) of 11.5°, 18.2°, 19.3°, 22.3°, 23.0° and 33.3° in powder X-ray (Cu—Kα) diffraction.

In addition, the present invention relates to a reduced coenzyme Q10 crystal showing characteristic absorption peaks at 862±1 $cm^{-1}$ and 881±1 $cm^{-1}$ in infrared spectroscopic analysis by a tablet method (KBr method).

Furthermore, the present invention also relates to a reduced coenzyme Q10 crystalline solid containing the reduced coenzyme Q10 crystal, and a method for producing the solid.

Furthermore, the present invention also relates to use of the reduced coenzyme Q10 crystal, and a composition containing the reduced coenzyme Q10 crystal and the reduced coenzyme Q10 crystalline solid.

The present specification encompasses the specification and/or drawings in JP Patent Application No. 2011-141028 which serves as the basis of the priority of the present application.

Advantageous Effects of Invention

Since the crystal form of reduced coenzyme Q10 first found in the present invention is much more stable and also more excellent in other physical properties than that of the conventionally known reduced coenzyme Q10 crystal, the crystal form not only overcomes conventional drawbacks of reduced coenzyme Q10, which is very easily oxidized and has limitations in terms of use, but also can provide new applications and utilizing methods of reduced coenzyme Q10. In addition, the reduced coenzyme Q10 crystal of the present invention and the crystalline solid containing the crystal are excellent in that not only they have excellent physical properties in the stable form but also production efficiencies thereof are high.

DESCRIPTION OF EMBODIMENTS

Figure 1:
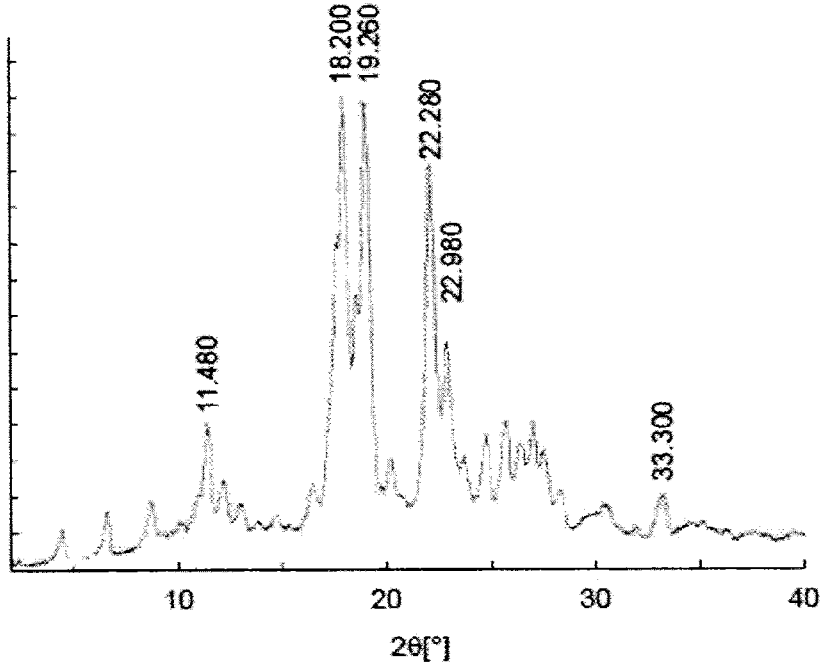
FIG. 1 is a powder X-ray diffraction spectrum of the reduced coenzyme Q10 crystal of Example 1 according to the present invention.

Hereinafter, the present invention will be described in detail. The "reduced coenzyme Q10" herein may partially include oxidized coenzyme Q10 as long as it includes reduced coenzyme Q10 as a main component. The "main component" herein means that it is included in a proportion of, for example, 60% by weight or more, usually 70% by weight or more, preferably 80% by weight or more, more preferably 90% by weight or more, further preferably 95% by weight or more, particularly preferably 98% by weight or more.

The reduced coenzyme Q10 crystal of the present invention is a reduced coenzyme Q10 crystal containing a novel crystal form, which has distinctly different physical properties and crystal structure from those of the conventionally known reduced coenzyme Q10 crystal, as described below.

The reduced coenzyme Q10 crystal of the present invention has an endothermic peak indicating crystal melting at 54±2° C., as measured at a rate of temperature rise of 5° C./min by differential scanning calorimetry (DSC). Such a temperature value is clearly higher than the temperature (50±1° C.) of an endothermic peak shown by the conventionally known reduced coenzyme Q10 crystal under the same condition (rate of temperature rise: 5° C./min). In addition, in the case of being measured in the same manner at a rate of temperature rise of 1° C./min, the reduced coenzyme Q10 crystal of the present invention shows an endothermic temperature peak at 52±2° C. It is to be noted that the conventionally known reduced coenzyme Q10 crystal shows an endothermic peak at 48±1° C. under the same condition (rate of temperature rise: 1° C./min).

Furthermore, the reduced coenzyme Q10 crystal of the present invention exhibits such physical properties that the solubility thereof in n-hexane at a temperature of 25° C. is, at most, 15% by weight or less, preferably 12% by weight or less, and more preferably 10% by weight or less. The solubility is clearly lower than the solubility (30% by weight or more) exhibited by the conventionally known reduced coenzyme Q10 crystal. In addition, the reduced coenzyme Q10 crystal of the present invention has the same tendency observed also with respect to a solubility thereof in a solvent other than hexane, and, for example, the solubility thereof in ethanol at a temperature of 30° C. is, at most, less than 4% by weight, preferably 3.5% by weight or less, and more preferably 3% by weight or less. This is lower than the solubility (4% by weight or more) exhibited by the conventionally known reduced coenzyme Q10 crystal.

Since the reduced coenzyme Q10 crystal of the present invention exhibits such properties that it has a higher melting point and a lower solubility than those of the conventionally known reduced coenzyme Q10 crystal, it is not only a crystal polymorph having a different crystal structure from that of the conventionally known reduced coenzyme Q10 crystal, namely, a novel reduced coenzyme Q10 crystal polymorph (or a crystal containing the crystal polymorph), but also a crystal of a stable form. The reduced coenzyme Q10 crystal of the stable form of the present invention is stable to heat and has a low solubility, and therefore, the enhancement in yield at the time of crystallization is expected.

In addition, the reduced coenzyme Q10 crystal of the present invention is also characterized by the following powder X-ray diffraction pattern and/or IR absorption pattern.

Specifically, the reduced coenzyme Q10 crystal of the present invention shows characteristic peaks at diffraction angles (2θ±0.2°) of 11.5°, 18.2°, 19.3°, 22.3°, 23.0° and 33.3° in powder X-ray diffraction (XRD) using Cu—Kα-ray as an X-ray source. The reduced coenzyme Q10 crystal shows characteristic strong diffraction peaks particularly at 18.2°, 19.3° and 22.3°, and is further characterized by showing strong diffraction peaks at 18.2° and 22.3°. It is to be noted that the intensity of a powder X-ray diffraction peak is known to vary under the influence of crystalline orientation and a part or all of the intensities of characteristic peaks may not be sufficient depending on the measurement. However, this is a common phenomenon in XRD analysis, and it is encompassed within the present invention. FIG. 1 shows an example of a result of the powder X-ray diffraction measurement of the reduced coenzyme Q10 crystal of the present invention. The XRD diffraction pattern shown in FIG. 1 is entirely different from the diffraction pattern of the conventionally known crystal (Patent Literature 4 and the like) in that the above characteristic peaks are observed, and it is clear that the reduced coenzyme Q10 crystal of the present invention shown in FIG. 1 is a novel crystal polymorph of reduced coenzyme Q10.

Figure 2:
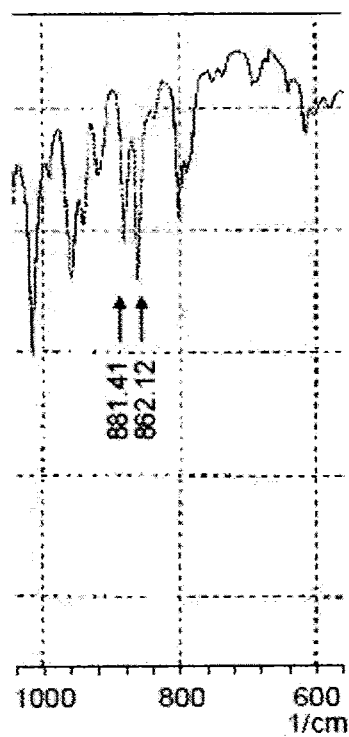
FIG. 2 is an infrared spectroscopic spectrum of the reduced coenzyme Q10 crystal of Example 1 according to the present invention.

Alternatively, the reduced coenzyme Q10 crystal of the present invention shows characteristic absorption peaks at around 862±1 $cm^{-1}$ and 881±1 $cm^{-1}$ in infrared spectroscopic (IR) analysis by a tablet method (KBr method). The peaks at around 862±1 $cm^{-1}$ and 881±1 $cm^{-1}$ are characteristic absorption peaks of two peaks having the same degree of intensity. The conventionally known reduced coenzyme Q10 crystal does not have absorption peaks of two peaks at these positions, and it is thus clearly indicated that the reduced coenzyme Q10 crystal of the present invention has novel reduced coenzyme Q10 crystal polymorph different from the conventionally known crystal form. FIG. 2 shows an example of a result of the infrared spectroscopic analysis measurement of the reduced coenzyme Q10 crystal of the present invention.

The reduced coenzyme Q10 crystal of the present invention may coexist with the conventionally known reduced coenzyme Q10 crystal as long as it contains novel reduced coenzyme Q10 crystal polymorph having the DSC endothermic peak, XRD diffraction pattern and/or IR absorption pattern. A crystalline solid also falls within the present invention as long as it contains the reduced coenzyme Q10 crystal of the present invention, whether other solid form of reduced coenzyme Q10 coexists or not. Herein, the novel reduced coenzyme Q10 crystal polymorph included in the reduced coenzyme Q10 crystal of the present invention is more stable than the conventionally known crystal form, and therefore, if the novel reduced coenzyme Q10 crystal polymorph is present in the reduced coenzyme Q10 crystal and crystalline solid of the present invention even in a small amount, all can also be transited to the novel reduced coenzyme Q10 crystal polymorph over time.

From such a viewpoint, the content of the novel reduced coenzyme Q10 crystal polymorph in the reduced coenzyme Q10 crystal and crystalline solid of the present invention is not particularly limited, but the content is, for example, 0.1% by weight or more, usually 1% by weight or more, preferably 10% by weight or more, more preferably 20% by weight or more, further preferably 30% by weight or more, particularly preferably 50% by weight or more, especially 70% by weight or more, and in particular 85% by weight or more. When the lower limit of the content of the novel reduced coenzyme Q10 crystal polymorph is each of the above values, the upper limit corresponding to each lower limit is naturally 100% by weight. Whether the novel reduced coenzyme Q10 crystal polymorph and the conventionally known crystal form are present in the reduced coenzyme Q10 crystal and crystalline solid of the present invention in a mixed state, or not, and the proportions thereof can be known by, for example, performing a measurement at a rate of temperature rise of 1° C./min and in a sample amount of 5±2 mg using DSC. Since the respective endothermic peaks indicating melting, of the conventionally known reduced coenzyme Q10 crystal and the novel reduced coenzyme Q10 crystal polymorph are clearly separated under the conditions, and the sizes of the peaks thereof correlate with a ratio thereof mixed, the presence of the novel reduced coenzyme Q10 crystal polymorph and the content thereof can be definitely determined even when the conventionally known reduced coenzyme Q10 crystal is mixed in the reduced coenzyme Q10 crystal and crystalline solid of the present invention.

Furthermore, the reduced coenzyme Q10 crystal of the present invention exhibits an excellent stability to oxygen. While reduced coenzyme Q10 has been conventionally known to be easily oxidized by oxygen molecule in air, the novel reduced coenzyme Q10 crystal polymorph found in the present invention and the reduced coenzyme Q10 crystal including the same as a main component exhibit a very high stability in the state where no measure is taken for protection against oxygen in air at all, as indicated in Examples described later. This phenomenon cannot be expected from properties of the conventionally known reduced coenzyme Q10 crystal and a composition containing the crystal. In addition, the reduced coenzyme Q10 crystal polymorph of the present invention exerts a high oxidation stability even in the coexistence with the conventionally known reduced coenzyme Q10 crystal and other amorphous component, and the reduced coenzyme Q10 crystalline solid of the present invention also exhibits oxidation stability such an extent that cannot be considered from conventional findings. The oxidation stability of the reduced coenzyme Q10 crystal and crystalline solid of the present invention depends on the content of the novel reduced coenzyme Q10 crystal polymorph in the crystal or crystalline solid and storage conditions, and cannot be generally said, but the retention rate (%) of reduced coenzyme Q10 after, for example, storage at 25° C. in air under light shielding conditions for a predetermined period is generally about 60% or more, preferably about 80% or more, further preferably about 85% or more, and particularly preferably 90% or more. The retention rate as used herein means a value determined as a ratio of the absolute amount of reduced coenzyme Q10 after storage for a predetermined period (or a concentration in the crystalline solid)/the absolute amount of reduced coenzyme Q10 in a composition before storage (or a concentration in the crystalline solid). In addition, the predetermined period is not particularly limited, but it is, for example, 1 week, preferably 2 weeks, and more preferably 4 weeks.

Then, a method for producing the reduced coenzyme Q10 crystal and crystalline solid of the present invention will be described.

The reduced coenzyme Q10 crystal of the present invention and the reduced coenzyme Q10 crystalline solid containing the crystal of the present invention can be produced by performing cooling crystallization and a subsequent treatment under specified conditions. For example, they can be produced by performing cooling crystallization of reduced coenzyme Q10 in an aliphatic hydrocarbon solvent at a given temperature, preferably 25° C. or higher, more preferably in a range from 25 to 70° C., further preferably 25 to 60° C. to precipitate a reduced coenzyme Q10 crystal or a crystalline solid, and then keep it at a given temperature for a given time or more, preferably 25° C. or higher for 24 hours or more, more preferably in a range from 25 to 70° C. for 24 hours to 3 years, further preferably 25 to 60° C. for 24 hours to 6 months. Under such conditions, the conventionally known reduced coenzyme Q10 crystal can be used as a seed crystal, or a seed crystal may not be used at the time of crystallization. As the reduced coenzyme Q10 for use in crystallization, one obtained by a conventionally known method can be used, a reaction liquid containing reduced coenzyme Q10 obtained from oxidized coenzyme Q10 by a known reduction method or an extraction liquid of reduced coenzyme Q10 obtained by a known method or the like can be utilized after being subjected to solvent replacement or the like if necessary, or one obtained by dissolving a purified reduced coenzyme Q10 powder or a commercially available reduced coenzyme Q10 powder or the like in an aliphatic hydrocarbon-based solvent can be used. The solvent for use in crystallization and a subsequent treatment is not particularly limited as long as it is an aliphatic hydrocarbon, but it is preferably hexane, heptane, or octane, and particularly preferably hexane. The crystallization concentration and the retention time after crystallization can be appropriately determined in consideration of the solubility of reduced coenzyme Q10 in the solvent or the like so that an objective reduced coenzyme Q10 crystal or crystalline solid is obtained. When n-hexane is used for the solvent, the object can be obtained by preparing a solution of reduced coenzyme Q10 in hexane in a concentration of 40% with warming, then subjecting it to cooling crystallization to 25° C. to precipitate a reduced coenzyme Q10 crystal, and then keeping the precipitated reduced coenzyme Q10 crystal in the solvent as it is at that temperature for 24 hours or more, preferably 48 hours or more, further preferably 96 hours or more. The upper limit of the retention time is not limited, and while it may be several years until the objective reduced coenzyme Q10 crystal or crystalline solid is obtained, it is preferably within 6 months. In the keeping step, a mixed liquid of the precipitated reduced coenzyme Q10 crystal and the solvent may be stirred or still stand, but is preferably stirred. Herein, there may be a case where the reduced coenzyme Q10 crystal and crystalline solid of the present invention in which the conventionally known reduced coenzyme Q10 crystal and the novel reduced coenzyme Q10 crystal polymorph are mixed is obtained, and a case where the reduced coenzyme Q10 crystal of the present invention including only the novel reduced coenzyme Q10 crystal polymorph is obtained, depending on the retention time, and both of the cases fall within the method for the production of the present invention, as described above.

The reduced coenzyme Q10 crystal of the present invention and the reduced coenzyme Q10 crystalline solid containing the crystal of the present invention can also be produced by subjecting a reduced coenzyme Q10 crystal or crystalline solid as it is (in a powder state) without dissolving it in the solvent or the like, to heating and/or shearing and the like (heating/shearing step). The crystal polymorph of the reduced coenzyme Q10 crystal or crystalline solid for use as a raw material in the above method is not particularly limited. Even if only the conventionally known reduced coenzyme Q10 crystal or crystalline solid is used at the time of crystallization, it can be certainly converted to the reduced coenzyme Q10 crystal or crystalline solid of the present invention by performing the specified heating/shearing step.

In the heating/shearing step, a reduced coenzyme Q10 crystal or crystalline solid is sheared, for example, in a powder state. As the means for shearing a reduced coenzyme Q10 crystal or crystalline solid, a combination of a shearing apparatus and a reactor which are common in the art can be used. For example, a reduced coenzyme Q10 crystal or crystalline solid is placed in a reactor, and stirred using an anchor blade, a screw blade, a helical ribbon blade, a broad paddle blade, a multi-stage tilt paddle blade or a three-way sweptback blade, or other stirring blade having a surface closely opposite to a wall surface; or a grindstone or mortar apparatus, or an apparatus capable of providing a shearing force, such as a ball mill or a bead mill, may be used.

In addition, in order to obtain the reduced coenzyme Q10 crystal or crystalline solid of the present invention, a reduced coenzyme Q10 crystal or crystalline solid may be subjected to not only a shearing treatment as described above but also a heating treatment at a predetermined temperature in a powder state. The temperature of the heating treatment is preferably such a temperature that allows reduced coenzyme Q10 not to be completely molten, and a high temperature as much as possible, and is specifically preferably in a range from 45 to 48° C. and more preferably in a range from 46 to 47° C. The pressure at the heating treatment is not particularly limited, and may be under reduced pressure, under pressure, or under ordinary pressure as long as reduced coenzyme Q10 is not completely molten. The time of the heating treatment is not particularly limited, and may be appropriately set based on the amount of the reduced coenzyme Q10 crystal or crystalline treated and/or a desirable conversion. The time is, for example, 3 hours or more, preferably 6 hours or more, more preferably 8 hours or more, and further preferably 12 hours or more. In addition, the heating treatment and the shearing treatment may be combined with each other. The heating treatment and/or shearing treatment under the above conditions make(s) it possible to obtain the reduced coenzyme Q10 crystal or crystalline solid having novel crystal polymorph, of the present invention.

In the above method, the heating/shearing step can also be performed following a step of drying the reduced coenzyme Q10 crystal or crystalline solid subjected to solid-liquid separation after crystallization of reduced coenzyme Q10. In this case, in the heating/shearing step, the solvent and the like used for the crystallization and/or subsequent treatment may remain in the reduced coenzyme Q10 crystal or crystalline solid in a slight amount.

On the other hand, if the novel reduced coenzyme Q10 crystal polymorph or the reduced coenzyme Q10 crystal containing it of the present invention can be produced or acquired once, the novel reduced coenzyme Q10 crystal polymorph or the reduced coenzyme Q10 crystal of the present invention can also be added as a seed crystal at the time of performing crystallization operation to thereby produce the reduced coenzyme Q10 crystal or crystalline solid of the present invention under common conditions. In this case, such production can be performed using at least one of cooling crystallization, poor solvent addition crystallization, concentration crystallization, melting crystallization, and the like. A preferable crystallization method is a method of performing cooling crystallization, or a combination method of cooling crystallization with other crystallization method.

In the case of a crystallization method using a seed crystal, a solvent for such crystallization is not particularly limited, and an arbitrary solvent can be used therefor. On the other hand, in the case of melting crystallization, a solvent is not always used. Examples of the solvent for use in crystallization include hydrocarbons, aliphatic esters, ethers, nitriles, alcohols, ketones, nitrogen compounds, sulfur compounds, and water. Examples of the hydrocarbons include, but not particularly limited to, aliphatic hydrocarbon, aromatic hydrocarbon and halogenated hydrocarbon. The aliphatic hydrocarbon to be used may be cyclic or acyclic, may be saturated or unsaturated, and is not particularly limited, but is usually one having 3 to 20 carbon atoms, preferably one having 5 to 12 carbon atoms. Specific examples thereof include propane, butane, isobutane, pentane, 2-methylbutane, cyclopentane, 2-pentene, hexane, 2-methylpentane, 2,2-dimethylbutane, 2,3-dimethylbutane, methylcyclopentane, cyclohexane, 1-hexene, cyclohexene, heptane, 2-methylhexane, 3-methylhexane, 2,3-dimethylpentane, 2,4-dimethylpentane, methylcyclohexane, 1-heptene, octane, 2,2,3-trimethylpentane, isooctane, ethylcyclohexane, 1-octene, nonane, 2,2,5-trimethylhexane, 1-nonene, decane, 1-decene, p-menthane, undecane and dodecane. The aromatic hydrocarbon to be used is not particularly limited, but is usually one having 6 to 20 carbon atoms, preferably one having 6 to 12 carbon atoms, more preferably one having 7 to 10 carbon atoms. Specific examples thereof include benzene, toluene, xylene, o-xylene, m-xylene, p-xylene, ethylbenzene, cumene, mesitylene, tetralin, butylbenzene, p-cymene, cyclohexylbenzene, diethylbenzene, pentylbenzene, dipentylbenzene, dodecylbenzene and styrene.

The halogenated hydrocarbon to be used may be cyclic or acyclic, may be saturated or unsaturated, and is not particularly limited, but is preferably acyclic one. More preferred is chlorinated hydrocarbon or fluorinated hydrocarbon, and further preferred is chlorinated hydrocarbon. In addition, to be used is one having 1 to 6 carbon atoms, preferably one having 1 to 4 carbon atoms, more preferably one having 1 to 2 carbon atoms. Specific examples thereof include dichloromethane, chloroform, carbon tetrachloride, 1,1-dichloroethane, 1,2-dichloroethane, 1,1,1-trichloroethane, 1,1,2-trichloroethane, 1,1,1,2-tetrachloroethane, 1,1,2,2-tetrachloroethane, pentachloroethane, hexachloroethane, 1,1-dichloroethylene, 1,2-dichloroethylene, trichloroethylene, tetrachloroethylene, 1,2-dichloropropane, 1,2,3-trichloropropane, chlorobenzene and 1,1,1,2-tetrafluoroethane.

Examples of the aliphatic esters include, but not particularly limited to, propionic acid ester, acetic acid ester and formic acid ester. Preferred is acetic acid ester or formic acid ester, and more preferred is acetic acid ester. An ester group includes, but not particularly limited to, an alkyl ester having 1 to 8 carbon atoms and an aralkyl ester having 1 to 8 carbon atoms, and is preferably an alkyl ester having 1 to 6 carbon atoms and more preferably an alkyl ester having 1 to 4 carbon atoms. Examples of the propionic acid ester include methyl propionate, ethyl propionate, butyl propionate, and isopentyl propionate. Examples of the acetic acid ester include methyl acetate, ethyl acetate, propyl acetate, isopropyl acetate, butyl acetate, isobutyl acetate, sec-butyl acetate, pentyl acetate, isopentyl acetate, sec-hexyl acetate, cyclohexyl acetate, and benzyl acetate. Examples of the formic acid ester include methyl formate, ethyl formate, propyl formate, isopropyl formate, butyl formate, isobutyl formate, sec-butyl formate, and pentyl formate.

The ethers to be used may be cyclic or acyclic, may be saturated or unsaturated, and are not particularly limited, but are preferably saturated ethers. Ethers having 3 to 20 carbon atoms are usually used, ethers having 4 to 12 carbon atoms are preferably used, and ethers having 4 to 8 carbon atoms are more preferably used.

Specific examples thereof include diethylether, methyl tert-butyl ether, dipropylether, diisopropylether, dibutylether, dihexylether, ethylvinylether, butylvinylether, anisole, phenetole, butylphenylether, methoxytoluene, dioxane, furan, 2-methylfuran, tetrahydrofuran, tetrahydropyran, ethyleneglycol dimethylether, ethyleneglycol diethylether, ethyleneglycol dibutylether, ethyleneglycol monomethylether, ethyleneglycol monoethylether and ethyleneglycol monobutylether.

The nitriles to be used may be cyclic or acyclic, may be saturated or unsaturated, and are not particularly limited, but are preferably saturated nitriles. Nitriles having 2 to 20 carbon atoms are usually used, nitriles having 2 to 12 carbon atoms are preferably used, and nitriles having 2 to 8 carbon atoms are more preferably used.

Specific examples thereof include acetonitrile, propionitrile, malononitrile, butyronitrile, isobutyronitrile, succinonitrile, valeronitrile, glutaronitrile, hexanenitrile, heptylcyanide, octylcyanide, undecanenitrile, dodecanenitrile, tridecanenitrile, pentadecanenitrile, stearonitrile, chloroacetonitrile, bromoacetonitrile, chloropropionitrile, bromopropionitrile, methoxyacetonitrile, methyl cyanoacetate, ethyl cyanoacetate, tolunitrile, benzonitrile, chlorobenzonitrile, bromobenzonitrile, cyanobenzoic acid, nitrobenzonitrile, anisonitrile, phthalonitrile, bromotolunitrile, methylcyanobenzoate, methoxybenzonitrile, acetylbenzonitrile, naphthonitrile, biphenylcarbonitrile, phenylpropionitrile, phenylbutyronitrile, methylphenylacetonitrile, diphenylacetonitrile, naphthylacetonitrile, nitrophenylacetonitrile, chlorobenzylcyanide, cyclopropanecarbonitrile, cyclohexanecarbonitrile, cycloheptanecarbonitrile, phenylcyclohexanecarbonitrile and tolylcyclohexanecarbonitrile.

The alcohols to be used may be cyclic or acyclic, may be saturated or unsaturated, and are not particularly limited, but are preferably saturated alcohols. Examples of a monohydric alcohol include one having 1 to 20 carbon atoms, preferred is one having 1 to 12 carbon atoms, more preferred is one having 1 to 6 carbon atoms, further preferred is one having 1 to 5 carbon atoms, particularly preferred is one having 1 to 4 carbon atoms, and especially preferred is one having 1 to 3 carbon atoms. Most preferred is a monohydric alcohol having 2 to 3 carbon atoms. In addition, a dihydric alcohol having 2 to 5 carbon atoms, preferably 2 to 3 carbon atoms, or a trihydric alcohol having 3 carbon atoms or the like is also suitably used. Among them, a monohydric alcohol having 1 to 5 carbon atoms is an alcohol having high compatibility with water, and is suitably used in the case of being used as a mixed solvent with water. Examples of the monohydric alcohol include methanol, ethanol, 1-propanol, 2-propanol, 1-butanol, 2-butanol, isobutylalcohol, tert-butylalcohol, 1-pentanol, 2-pentanol, 3-pentanol, 2-methyl-1-butanol, isopentylalcohol, tert-pentylalcohol, 3-methyl-2-butanol, neopentylalcohol, 1-hexanol, 2-methyl-1-pentanol, 4-methyl-2-pentanol, 2-ethyl-1-butanol, 1-heptanol, 2-heptanol, 3-heptanol, 1-octanol, 2-octanol, 2-ethyl-1-hexanol, 1-nonanol, 1-decanol, 1-undecanol, 1-dodecanol, allylalcohol, propargylalcohol, benzyl alcohol, cyclohexanol, 1-methylcyclohexanol, 2-methylcyclohexanol, 3-methylcyclohexanol and 4-methylcyclohexanol. Examples of the dihydric alcohol include 1,2-ethanediol, 1,2-propanediol, 1,3-propanediol, 1,2-butanediol, 1,3-butanediol, 1,4-butanediol, 2,3-butanediol and 1,5-pentanediol. Examples of the trihydric alcohol include glycerin.

The ketones to be used are not particularly limited, and are suitably ketones having 3 to 6 carbon atoms. Specific examples thereof include acetone, methyl ethyl ketone, methyl butyl ketone, and methyl isobutyl ketone.

Examples of the nitrogen compounds include nitromethane, triethylamine, pyridine, formamide, N-methylformamide, N,N-dimethylformamide, N,N-dimethylacetamide and N-methylpyrrolidone, in addition to the above nitriles.

Examples of the sulfur compounds include dimethylsulfoxide and sulfolane.

Each of these solvents can be used with being mixed in a preferable proportion according to properties of each solvent in order to improve the conditions which affect crystallization conditions such as the solubility, crystallization concentration, yield, slurry properties and/or crystalline properties of reduced coenzyme Q10.

Even when any crystallization is performed, a conventionally known crystallization apparatus can be arbitrarily used, and for example, a bath equipped with a cooling jacket and a stirring apparatus (jacketed stirring bath), or a bath externally equipped with a heat exchanger for cooling, which allows a liquid in the bath to be circulated to perform cooling and mixing (external circulation type bath), or the like can be used.

The reduced coenzyme Q10 crystal and crystalline solid of the present invention, obtained by the above method, are recovered through a step of solid-liquid separation and drying or the like by a conventionally known method described in, for example, Patent Literature 2 or 3, if necessary. For example, pressure filtration or centrifugal filtration can be used for solid-liquid separation. In addition, the crystalline solid after drying can also be recovered by pulverization or classification (sieving), if necessary.

Herein, the crystallization, keeping, heating/shearing and work-up steps are preferably performed under a deoxygenated atmosphere. The deoxygenated atmosphere can be achieved by replacement with an inert gas, reduced pressure or boiling, or a combination thereof. Replacement with an inert gas, namely, an inert gas atmosphere is at least suitably used. Examples of the inert gas include nitrogen gas, helium gas, argon gas, hydrogen gas, and carbon dioxide, and preferred is nitrogen gas.

The reduced coenzyme Q10 crystal and crystalline solid of the present invention can be used in applications such as foods, nutritional functional foods, specified health foods, nutritious supplements, nutrients, animal drugs, drinks, feeds, cosmetics, medicaments, treating drugs, preventing drugs, or pet foods.

The reduced coenzyme Q10 crystal and crystalline solid of the present invention can be if necessary combined with an excipient, a disintegrator, a lubricant, a binder, an antioxidant, a colorant, an anticoagulation agent, an absorption promoter, a solubilizer, a stabilizer, a viscosity modifier, oil and fat or a surfactant, or an active ingredient other than reduced coenzyme Q10, each acceptable for applications such as medicaments, foods, feeds, or cosmetics, to afford a composition containing the reduced coenzyme Q10 crystal of the present invention. Examples of the active substance other than reduced coenzyme Q10 include amino acid, vitamin, mineral, polyphenol, organic acid, saccharide, peptide, and protein.

The composition of the present invention can be used as it is, but can be suitably used with being further processed to a preparation for oral administration, such as a capsule (hard capsule or soft capsule), a tablet or a coating agent (for example, sugar-coated tablet), or a syrup or a drink, or can be used with being further processed to a preparation for creams, suppositories or dentifrices. Particularly preferred is a capsule, especially, a soft capsule. A capsule base material is not particularly limited, and not only gelatin derived from cow bone, cowhide, pig skin, fish skin, or the like, but also other base material (for example, a thickening stabilizer usable as a food additive, for example, an article derived from seaweed such as carrageenan or alginic acid, and an article derived from a plant seed such as locust bean gum or guar gum, and a producing agent including celluloses) can be used.

Since the reduced coenzyme Q10 crystal of the present invention and the crystalline solid containing the crystal are more excellent in stability than the conventionally known reduced coenzyme Q10 crystal, the temperature thereof can be increased during, for example, increasing of the pressure at tableting, or formulating of a high-viscosity liquid, to improve fluidity, thereby making it possible to enhance the production efficiency of a formulation or composition containing reduced coenzyme Q10.

Furthermore, the reduced coenzyme Q10 crystal of the present invention has a lower electrostatic charge, thereby extremely less likely causing sticking of the crystal to a spatula, or the inner wall of a glass bottle, a production apparatus or a packaging material, or scattering during handling of the crystal by weighing or the like than the case of the conventionally known reduced coenzyme Q10 crystal. Accordingly, the reduced coenzyme Q10 crystal of the present invention is excellent in that it hardly causes the deterioration in production efficiency due to the sticking to equipment, and the like even at the time of production, and it has small problems in terms of safety, such as dust explosion, and contamination of facilities/workers.

EXAMPLES

Hereinafter, the present invention will be more specifically described with reference to Examples. However, the technical scope of the present invention is not intended to be limited to these Examples.

Hereinafter, the present invention will be described in more detail with reference to Examples, but the present invention is not intended to be limited only to these Examples. Herein, measurement conditions of differential scanning calorimetry (DSC), powder X-ray diffraction (XRD) and infrared spectroscopic (IR) analysis in Examples are as follows.

| (DSC Measurement Conditions) | |
| --- | --- |
| Apparatus: | DSC 6220 manufactured by SII Nano Technology Inc. |
| Sample container: | Aluminum pan & cover (SSC000C008) |
| Rate of temperature rise: | 5° C./min or 1° C./min |
| Amount of sample: | 10 ± 5 mg at a rate of temperature rise of 5° C./min<br>5 ± 2 mg at a rate of temperature rise of 1° C./min |

| (XRD Measurement Conditions) | |
| --- | --- |
| Apparatus: | MiniFlexII manufactured by Rigaku Corporation |
| X-ray used: | Cu—Kα-ray |
| Intensity: | 30 kV, 15 mA |
| Angle: | 2θ = 2 to 60° |

-continued

| (XRD Measurement Conditions) | |
|---|---|
| Scanning rate: | 2°/min |
| Divergence slit (DS): | 1.25° |
| Scatter slit (SS): | 1.25° |
| Receiving slit (RS): | 0.3 mm |

| (IR Measurement Conditions) | |
|---|---|
| Apparatus: | FTIR-8400S manufactured by Shimadzu Corporation |
| Resolution: | 4 cm$^{-1}$ |
| Apodization: | Happ-Genzel |
| Cumulative number: | 40 |
| Measurement method: | Tablet method (KBr method) |

Example 1

The inside of a 300 mL reaction flask (made of heat resistant glass) was replaced with nitrogen, and thereafter 40 g of commercially available reduced coenzyme Q10 (produced by Kaneka Corporation, conventionally known reduced coenzyme Q10 crystal) and 60 g of n-hexane were charged thereto and warmed to 40° C. with stirring to completely dissolve the reduced coenzyme Q10 in n-hexane. The solution was cooled to 25° C. at a cooling rate of 10° C./hour, then kept at 25° C. for 96 hours while being continuously stirred, and subjected to filtration and drying (drying under reduced pressure, 20 to 40° C.) to provide a crystal. From the result of analysis by DSC, the crystal was confirmed to have an endothermic peak indicating melting at 54.2° C. during temperature rise at a rate of 5° C./min, and an endothermic peak indicating melting at 51.6° C. during temperature rise at a rate of 1° C./min. In addition, as the result of analysis by powder X-ray diffraction, characteristic peaks at diffraction angles (2θ±0.2°) of 11.50°, 18.26°, 19.30°, 22.30°, 23.00° and 33.14° were observed as shown in FIG. 1. Furthermore, from the result of analysis by IR, the crystal had characteristic absorption peaks at 862±1 cm$^{-1}$ and 881±1 cm$^{-1}$ as shown in FIG. 2, unlike to the result of the conventionally known reduced coenzyme Q10 crystal. From the above analysis results, it was confirmed that the reduced coenzyme Q10 crystal obtained in the present Example was in a different crystal form from the conventionally known reduced coenzyme Q10 crystal. The solubility of the resulting crystal in hexane was measured, and found to be 9% by weight at a temperature of 25° C. Herein, the resulting crystal did not exhibit sticking property particularly due to its electrostatic charge in the pulverization process of the crystal by a mortar, performed as a pretreatment of powder X-ray measurement, and had particularly no problem during collection thereof by a spatula made of stainless.

Example 2

The inside of a 300 mL reaction flask (made of heat resistant glass) was replaced with nitrogen, and thereafter 40 g of commercially available reduced coenzyme Q10 (produced by Kaneka Corporation, conventionally known reduced coenzyme Q10 crystal) and 60 g of n-hexane were charged thereto and warmed to 40° C. with stirring to completely dissolve the reduced coenzyme Q10 in n-hexane. The solution was cooled to 25° C. at a cooling rate of 10° C./hour, and then 0.4 g of the reduced coenzyme Q10 crystal obtained in Example 1 (the reduced coenzyme Q10 crystal of the present invention) was added as a seed crystal. After the addition, the resultant was kept at 25° C. for 24 hours, and immediately thereafter, subjected to filtration and drying to provide a crystal. From the result of analysis by DSC, the crystal was confirmed to have an endothermic peak indicating melting at 53.9° C. during temperature rise at a rate of 5° C./min. In addition, as the result of analysis by powder X-ray diffraction, the resulting crystal showed a diffraction pattern of the reduced coenzyme Q10 crystal of the present invention, as in Example 1.

Example 3

The inside of a 300 mL reaction flask (made of heat resistant glass) was replaced with nitrogen, and thereafter 4 g of commercially available reduced coenzyme Q10 (produced by Kaneka Corporation, conventionally known reduced coenzyme Q10 crystal) and 96 g of ethanol were charged thereto and warmed to 40° C. with stirring to completely dissolve the reduced coenzyme Q10 in ethanol. The solution was cooled to 30° C. at a cooling rate of 10° C./hour, and then 0.4 g of the reduced coenzyme Q10 crystal obtained in Example 1 (the reduced coenzyme Q10 crystal of the present invention) was added as a seed crystal. After the addition, the resultant was kept at 30° C. for 24 hours, and immediately thereafter, subjected to filtration and drying to provide a crystal. From the result of analysis by DSC, the crystal was confirmed to have an endothermic peak indicating melting at 52.0° C. during temperature rise at a rate of 5° C./min. In addition, as the result of analysis by powder X-ray diffraction, the resulting crystal showed a diffraction pattern of the reduced coenzyme Q10 crystal of the present invention, as in Example 1.

Comparative Example 1

Figure 3:
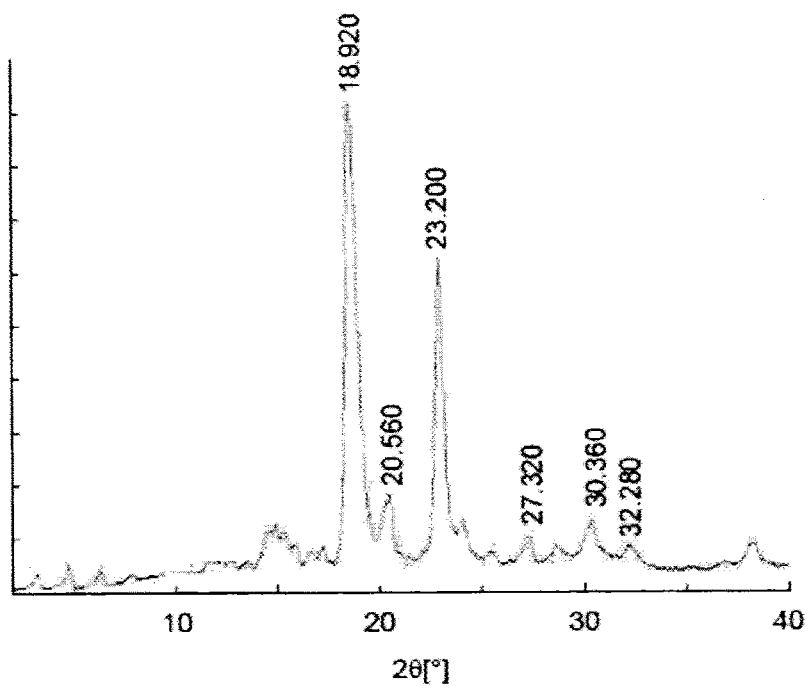
FIG. 3 is a powder X-ray diffraction spectrum of the conventionally known reduced coenzyme Q10 crystal of Comparative Example 1.
Figure 4:
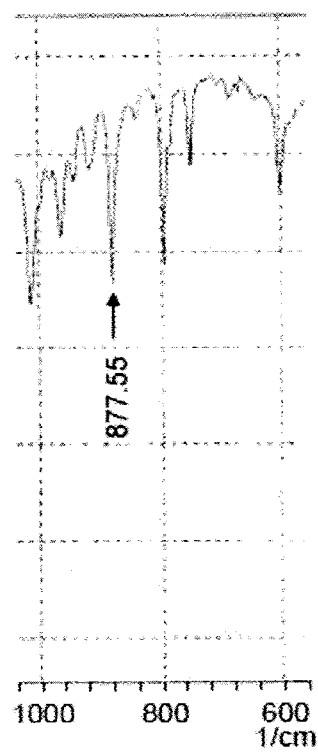
FIG. 4 is an infrared spectroscopic spectrum of the conventionally known reduced coenzyme Q10 crystal of Comparative Example 1.

The inside of a 300 mL reaction flask (made of heat resistant glass) was replaced with nitrogen, and thereafter 40 g of commercially available reduced coenzyme Q10 (produced by Kaneka Corporation, conventionally known reduced coenzyme Q10 crystal) and 60 g of n-hexane were charged thereto and warmed to 40° C. with stirring to completely dissolve the reduced coenzyme Q10 in n-hexane. The solution was cooled to 25° C. at a cooling rate of 10° C./hour, and then 0.4 g of the commercially available reduced coenzyme Q10 (conventionally known reduced coenzyme Q10 crystal) which was the same as that initially used, as a seed crystal. After the addition, the resultant was kept at 25° C. for 1 hour, subsequently cooled to 10° C. at a cooling rate of 1° C./hour, and immediately thereafter, subjected to filtration and drying (drying under reduced pressure, 20 to 40° C.) to provide a crystal. From the result of analysis by DSC, the crystal was confirmed to have an endothermic peak indicating melting at 50.4° C. during temperature rise at a rate of 5° C./min, and an endothermic peak indicating melting at 48.1° C. during temperature rise at a rate of 1° C./min. In addition, the result of analysis by powder X-ray diffraction of the resulting crystal is shown in FIG. 3, and the result of analysis by IR thereof is shown in FIG. 4.

The solubility of the resulting crystal in hexane was measured, and found to be 36.5% by weight at a temperature of 25° C. Herein, the resulting crystal exhibited remarkable sticking property due to its electrostatic charge in the pulverization process of the crystal by a mortar, performed as a pre-treatment of powder X-ray measurement, and was observed to be severely scattered to the environment during collection of the crystal by a spatula made of stainless.

Example 4

Each of the reduced coenzyme Q10 crystals obtained in Example 1 and Comparative Example 1 was placed in a glass bottle, and stored at 25° C. under light shielding in the state where the bottle was not lidded and was opened, and a weight ratio of reduced coenzyme Q10 to oxidized coenzyme Q10 was determined by the following HPLC analysis. The results are shown in Table 1.

| (HPLC Analysis Conditions) | |
| --- | --- |
| Column: | YMC-Pack (manufactured by YMC Co., Ltd.), 150 mm (length), 4.6 mm (inner diameter) |
| Mobile Phase: | methanol/hexane = 9/1 (v/v) |
| Detection wavelength: | 290 nm |
| Flow rate: | 1 ml/min |

TABLE 1

| | Weight ratio of reduced coenzyme Q10/oxidized coenzyme Q10 | |
| --- | --- | --- |
| Days | Crystal obtained in Example 1 | Crystal obtained in Comparative Example 1 |
| Before start | 98.8/1.2 | 99.5/0.5 |
| After 3 days | 98.6/1.4 | 97.7/2.3 |
| After 7 days | 97.8/2.2 | 84.0/16.0 |
| After 14 days | 95.7/4.3 | 50.2/49.8 |
| After 28 days | 93.1/6.9 | 28.2/71.8 |

From the above results, the reduced coenzyme Q10 of the present invention was confirmed to be very stable and be hardly oxidized even if no measure was particularly taken for protection against oxygen.

Example 5

In a 500 mL stainless reactor (manufactured by Taiatsu Techno Co., Ltd., inner diameter: 54 mm, depth: 225 mm) was placed 50 g of commercially available reduced coenzyme Q10 (produced by Kaneka Nutrients, conventionally known reduced coenzyme Q10 crystal), and the temperature in the reactor was raised to 46 to 47° C. with stirring under reduced pressure (pressure: 4 kPa) by a vacuum pump. An anchor blade (length of blade: 50 mm) was used for the stirring, and the rotation number of stirring was set to 300 rpm. This operation was continued for 55 hours, and then the powder X-ray diffraction analysis was performed. As a result, characteristic peaks were observed at diffraction angles (2θ±0.2°) of 11.44°, 18.14°, 19.10°, 22.22°, 23.08° and 33.24° as shown in FIG. 1, and it was thus confirmed that the resulting crystal form was different from that of conventionally known reduced coenzyme Q10.

Comparative Example 2

In a vacuum oven (VO-400 manufactured by As One Corporation) was placed 50 g of commercially available reduced coenzyme Q10 (produced by Kaneka Corporation, conventionally known reduced coenzyme Q10 crystal), and the temperature in the vacuum oven was raised to 42° C. with still standing under reduced pressure by a vacuum pump. This operation was continued for 98 hours, and then the powder X-ray diffraction analysis was performed. As a result, the diffraction peak pattern was the same as that of the conventionally known reduced coenzyme Q10 crystal, and no change was observed.

All publications, Patent Literatures and Patent Applications recited in the present specification are herein incorporated as reference as they are.

The invention claimed is:

1. A composition, comprising:
    a reduced coenzyme Q10 crystal showing characteristic peaks at diffraction angles in 2θ±0.2° of 11.5°, 18.2°, 19.3°, 22.3°, 23.0° and 33.3° in powder Cu—Kα X-ray diffraction,
    wherein the composition is in a solid form and the composition is at least one of food, nutritional functional food, specified health food, nutritious supplement, nutrient, animal drug, feed, cosmetic, medicament, treatment drug, prevention drug, and pet food.

2. The composition of claim 1, further comprising:
    at least one of an excipient, a disintegrator, a lubricant, a binder, an antioxidant, a colorant, an anticoagulation agent, an absorption promoter, and an active ingredient which is not reduced coenzyme Q10.

3. The composition of claim 2, wherein the active ingredient is at least one of amino acid, vitamin, mineral, polyphenol, organic acid, saccharide, peptide, and protein.

4. The composition of claim 1, which is in a form of a hard capsule.

5. The composition of claim 2, which is in a form of a hard capsule.

6. The composition of claim 3, which is in a form of a hard capsule.

7. The composition of claim 1, which is in a form of a tablet.

8. The composition of claim 2, which is in a form of a tablet.

9. The composition of claim 3, which is in a form of a tablet.

10. The composition of claim 1, which is in a form of a coated tablet.

11. The composition of claim 2, which is in a form of a coated tablet.

12. The composition of claim 3, which is in a form of a coated tablet.

* * * * *